United States Patent
Xu et al.

(10) Patent No.: US 9,491,943 B2
(45) Date of Patent: Nov. 15, 2016

(54) BIOENGINEERING STRAIN FOR PRODUCTION OF NOVEL MICROORGANISM-ORIGINATED FUNGICIDES AND USES THEREOF

(75) Inventors: Yuquan Xu, Shanghai (CN); Huifeng Shen, Shanghai (CN); Ya-Wen He, Shanghai (CN); Wanping Zhou, Shanghai (CN)

(73) Assignee: SHANGHAI JIAOTONG UNIVERSITY, Minhang District, Shanghai (CN)

( * ) Notice: Subject to any disclaimer, the term of this patent is extended or adjusted under 35 U.S.C. 154(b) by 0 days.

(21) Appl. No.: 14/356,636

(22) PCT Filed: Nov. 21, 2011

(86) PCT No.: PCT/CN2011/082531
§ 371 (c)(1),
(2), (4) Date: May 7, 2014

(87) PCT Pub. No.: WO2013/067719
PCT Pub. Date: May 16, 2013

(65) Prior Publication Data
US 2014/0309232 A1    Oct. 16, 2014

(30) Foreign Application Priority Data
Nov. 7, 2011   (CN) .......................... 2011 1 0347790

(51) Int. Cl.
| C12N 1/20 | (2006.01) |
| A01N 43/58 | (2006.01) |
| A01N 43/60 | (2006.01) |
| C12P 17/12 | (2006.01) |
| C12N 15/63 | (2006.01) |
| C12N 9/00 | (2006.01) |

(52) U.S. Cl.
CPC ................. *A01N 43/60* (2013.01); *C12N 1/20* (2013.01); *C12N 9/93* (2013.01); *C12N 15/63* (2013.01); *C12P 17/12* (2013.01); *C12Y 603/05004* (2013.01); *Y02P 20/52* (2015.11)

(58) Field of Classification Search
None
See application file for complete search history.

(56) References Cited

PUBLICATIONS

Chin-A-Woeng et al. Molecular Plant-Microbe Interactions, 14(8): 1006-1015, 2001.*
Chin-A-Woeng et al. Introduction of the phzH gene of *Pseudomonas* chlororaphis PCL 1391 extends the range of biocontrol ability of phenazine-1-carboxylic acid-producing *Pseudomonas* spp. strains, MPMI, 14(8): 1006-1015, 2001.*
van Rij et al. Influence of fusaric acid on phenazine-1carboxamide synthesis and gene expression of Pseudomonas chlororaphis strain PCL1391, Microbiology (2005), 151: 2805-2814.*

* cited by examiner

*Primary Examiner* — Iqbal H Chowdhury
(74) *Attorney, Agent, or Firm* — Global IP Services; Tianhua Gu

(57) ABSTRACT

The present invention relates to a bioengineering strain for production of novel microorganism-originated fungicides and uses thereof. The bioengineering strain for production of microorganism-originated fungicides of the present invention is obtained by transforming a phzH gene recombination expression plasmid into a strain producing phenazine-1-carboxylic acid, wherein the bioengineering strain produces phenazine-1-carboxamide. The present invention utilizes an existing strain producing phenazine-1-carboxylic acid to carry the phzH gene recombination expression plasmid, thereby achieving efficient expression of the phzH gene and transforming phenazine-1-carboxylic acid into phenazine-1-carboxamide. The present invention further discloses uses of the bioengineering strain, including a microorganism-originated fungicide produced by the bioengineering strain through fermentation, and preparation and application of the microorganism-originated fungicide. The antifungal activity of phenazine-1-carboxamide is not influenced by the acidity under which it is used, so that it has a stabilized antifungal activity and can be more effective in prophylaxis and treatment of crop diseases.

12 Claims, 2 Drawing Sheets

BIOENGINEERING STRAIN FOR PRODUCTION OF NOVEL MICROORGANISM-ORIGINATED FUNGICIDES AND USES THEREOF

CROSS REFERENCE TO RELATED PATENT APPLICATION

The present application is the US national stage of PCT/CN2011/082531 filed on Nov. 21, 2011, which claims the priority of the Chinese patent application No. 201110347790.7 filed on Nov. 7, 2011, which application is incorporated herein by reference.

FIELD OF THE INVENTION

The present invention pertains to the field of microorganism-originated pesticide production technologies, and more particularly, relates to a bioengineering strain for production of novel microorganism-originated fungicides and uses thereof.

BACKGROUND OF THE INVENTION

Loss attributable to crop diseases accounts for about 25-75% of the total production. For rice which is a major food crop in China, the annual plantation area is about 0.4 billion Mu. On the basis that the yield per Mu is 400 kg and the average reduction in output due to rice diseases is 10%, the annual economic loss will be as much as more than 30 billion RMB. As such, production of food crops is seriously threatened. So far, in addition to use of good seeds and modification of cultivation measures, plant diseases are mainly controlled by spraying chemical fungicides. Most of existing chemical fungicides are toxic and harmful to human body and animals to different degrees, and harmful components left over on the edible parts of plants result in potential threat to human health. This has received attention from the government and all levels of the society. Moreover, some chemical pesticides are hard to decompose, so that they are accumulated in the ecological system for a long period of time and pollute the environment, which is unfavorable to the sustainable developed of the social economy. Also, existing chemical pesticides are not very effective against some plant diseases. Therefore, while developing a new generation of chemical pesticides with endeavor, great efforts shall be put to study and develop high-performance biogenic pesticides that are safe, economic and highly compatible with the environment. At present, few types and amounts of biogenic pesticides are promoted and used in the production, and some types of biogenic pesticides result in resistance in plant pathogens due to long-time use, so that control efficiency is not ideal. In the case of rice sheath blight, pesticides for its control mainly depend on Jinggangmycin which is an old biogenic pesticide. However, after long-period use of nearly 40 years, some anastomosis groups of *Rhizoctonia solani* have become drug resistant. Moreover, Jinggangmycin is only effective against *Rhizoctonia solani* and has no obvious control effect against other pathogens, so it is greatly limited in respect of application scope.

A bio-pesticide growth-promoting antagonistic bacterium strain M18 has a high-efficiency, safe and broad-spectrum fungicidal effect on plant diseases. Also, it is well compatible with the environment and easily decomposed in the environment. The growth-promoting antagonistic bacterium strain M18 has been deposited at China General Microbiological Culture Collection Center, China Committee for Culture Collection of Microorganisms, a depository authority assigned by the State Intellectual Property Office of the PRC, the deposition No. being CGMCC NO.0462. Preparation and use of the bio-pesticide growth-promoting antagonistic bacterium M18 have been patented by the state with the patent no. ZL00119857.2. However, the bio-pesticide growth-promoting antagonistic bacterium strain M18 is a living bacterium agent whose mechanism mainly involves synthesis of an active component against plant diseases by strain M18 active bacteria to inhibit pathogens in crops, and the content of the synthesized active component is easily influenced by the metabolic regulation mechanism of the bacterium itself and environmental conditions. Therefore, M18 has a disadvantage of unstable control effect against plant diseases, so that it is hard for strain M18 to be applied in a large scale in agricultural production.

It has been proved that, the main active component of the growth-promoting antagonistic bacterium M18 for control of plant diseases is phenazine-1-carboxylic acid. Phenazine-1-carboxylic acid is extracted from the fermentation broth of growth-promoting antagonistic bacterium M18 to control crop diseases using the active component rather than the living bacterium, which also features high efficacy, safety, broad-spectrum and good compatibility with the environment. Also, this can overcome the deficiency that the growth-promoting antagonistic bacterium M18 is unstable in controlling diseases. However, synthesis of the active component phenazine-1-carboxylic acid through fermentation of the growth-promoting antagonistic bacterium M18 has a low titer which is only about 200 mg/L. How to increase fermentation titer and reduce cost becomes a bottleneck for development of this product. In recent years, we have made in-depth study on the regulation mechanism of synthesis of phenazine-1-carboxylic acid by the growth-promoting antagonistic bacterium M18 using molecular biological technologies. Based on this, through the means of genetic engineering, the two-component regulatory gene gacA in the genome of the growth-promoting antagonistic bacterium M18 is inactivated and mutated in a targeted manner, thereby obtaining M18G, a strain derived from M18. M18G greatly increases the yield of phenazine-1-carboxylic acid, so that the fermentation titer of phenazine-1-carboxylic acid reaches about 1500-1700 mg/L. The technical method of this study had been disclosed in Acta Microbiologica Sinica, Vol. 44, p 761-765 in 2004, and the title of the thesis is Differential Regulation of Phenazine-1-Carboxylic Acid and Pyoluteorin Production Mediated by Inactivated gacA in *Pseudomonas* sp. M18. In 2006, Chinese Patent (Patent No.: ZL200610023459.9) entitled Method for Preparation of Fungicides Using Growth-promoting Antagonistic Bacterium M18 provided a method for preparation of fungicides using growth-promoting antagonistic bacterium M18's derivative strains M18G and M18R, where the fungicide is prepared from the metabolites of microorganisms rather than living microorganisms, and the objective of increasing control effect is achieved by combination of the metabolites of the two derivative strains. In 2009, we further invented a method for production of phenazine-1-carboxylic acid by using bioengineering strain M18G carrying plasmid pME6032Phz, so that the fermentation titer of phenazine-1-carboxylic acid reaches 5700-6600 mg/L, which further reduces production cost and realizes large-scale application in agricultural production. This technology has been patented by the state with Patent No. ZL200910198664.2. Microorganism-originated fungicides with phenazine-1-carboxylic acid as a main component have been named Shenqinmycin by the Chinese pesticide denomination authority. Technical-grade Shenqinmycin and 1% Shenqinmycin suspension concentrate were granted with official registration nos. (Registration Nos.: PB20110314 and PB20110315) by the Ministry of Agriculture of the PRC in 2011. Shenqinmycin has been listed as one of the products promoted in the whole country during the 12th Five-Year Plan (Certificate No.: TG2011-002).

However, the control effect of phenazine-1-carboxylic acid against pathogens is closely related to the acidity (pH) under which it is used, and at pH 7.0, the antifungal activity of phenazine-1-carboxylic acid is only 20% of that at pH 5.0, so that the control effect of phenazine-1-carboxylic acid under alkaline conditions is greatly reduced. It is also found that, in the genomes of the growth-promoting antagonistic bacterium M18 and its derivative strain M18G, the phzH gene is a mutated and inactivated gene.

SUMMARY OF THE INVENTION

An objective of the present invention is, in view of the deficiencies of the prior art, to provide a bioengineering strain for production of novel microorganism-originated fungicides and application technologies thereof.

The present invention utilizes a strain producing phenazine-1-carboxylic acid to carry a recombination expression plasmid that can express phzH gene which is encoded to produce PhzH (glutamine phenazine-1-carboxylic acid amidotransferase), complement and add the copy number of the phzH gene to express in the engineering stain, thereby transforming phenazine-1-carboxylic acid into phenazine-1-carboxamide. The antifungal activity of phenazine-1-carboxamide is not influenced by the acidity under which it is used, so that it has a stabilized antifungal activity and can be more effective in prophylaxis and treatment of crop diseases.

The present invention first discloses a bioengineering strain for production of microorganism-originated fungicides, which is obtained by transforming a phzH gene recombination expression plasmid into a strain producing phenazine-1-carboxylic acid, wherein the bioengineering strain produces phenazine-1-carboxamide.

The present invention further discloses a method for constructing the bioengineering strain for production of microorganism-originated fungicides, comprising steps of:
1) amplifying a phzH gene segment;
2) inserting the amplified phzH gene segment into an expression vector to construct a phzH gene recombination expression plasmid;
3) transferring the constructed phzH gene recombination expression plasmid into a strain producing phenazine-1-carboxylic acid to construct the bioengineering strain for production of microorganism-originated fungicides.

The phzH gene recombination expression plasmid is a recombination expression plasmid cloned with a phzH gene segment. The phzH gene recombination expression plasmid can express the phzH gene in the strain producing phenazine-1-carboxylic acid where the phzH gene is encoded to produce PhzH (glutamine phenazine-1-carboxylic acid amidotransferase).

The phzH gene of the present invention comprises a coding region of the phzH gene and a noncoding region thereof.

The phzH gene segment may be a complete phzH gene or part of the phzH gene. The phzH gene segment of the present invention shall at least comprise a complete coding region of the phzH gene. Preferably, to be efficiently expressed into PhzH, the phzH gene segment comprises a complete coding region of the phzH gene and its 5'-end noncoding region. The 5'-end noncoding region comprised in the phzH gene segment may be a partial or complete 5'-end noncoding region of the phzH gene. The 5'-end noncoding region of the phzH gene comprised in the phzH gene segment shall facilitate expression of PhzH. Preferably, the 5'-end noncoding region comprised in the phzH gene segment comprises a polynucleotide segment starting from the first base upstream of the phzH gene translation initiation codon to the 683th base upstream of the codon.

Further, the PhzH is a PhzH of *Pseudomonas*, and the phzH gene segment is a phzH gene segment of *Pseudomonas*.

Preferably, the pseudomonad is *Pseudomonas aeruginosa* or *Pseudomonas chlororaphis*. Specifically, the pseudomonad is selected from *Pseudomonas aeruginosa* strains PAO1, LESB58, PA14, PUPa3, or a *Pseudomonas chlororaphis* stain PCL1391.

Further, the PhzH is from the *Pseudomonas aeruginosa* strain PAO1. As illustrated in the embodiments, the amino acid sequence of PhzH is SEQ ID NO: 1.

```
MCGLAGWVDY TRKLDDEFPA IFAMTDTLAL        60
RGPDAEGIWK HRNALLGHRR LAVIDLSGGV

QPMSYRFPTG QEVTLVYTGE VYNHDALRER       120
LRRAGHEFRT RSDTEVVLHA YLQWGERCCE

YLTGMFAFAV FDGRDGHLLL VRDRLGIKPL       180
YYARHREGLL FGSEIKSILA HPEFAARLDA

VGLVDLLTLS RGTSQTPFRE VQELLPGHLL       240
SWRPNSQAKL RRYWEVRRQE HADDLQSTVQ

RTRELVTRAL GAQLHADVPV CSLLSGGLDS       300
TALTGIAQRI AKAEHGGDIN SFSVDFVGQA

EQFRSDDLRP DQDQPFALLA AQYIGSRHRT       360
VLIDNAELVC ERAREEVFRA KDVPFTFGDM

DTSLHLMFGE IRRHSTVAIS GEGADELFGG       420
YGWFRDPQAV AAARFPWASR VRLPAGFIDA

GFNRRCDLLQ YQQASYDDGL RQVEHLAGDS       480
PEERRMREFS HLHLKRWMVL LLERKDRLSM

CNGLEVRVPY TDHELVEYVY NVPWSIKSRD       540
GEEKWLLKRA CADYVPEAVL KRRKSPYPTS

ANLGYERFLR GSVRRLLEDA VNPVFGIVSR       600
EFLAAELEHP EGYFNTQVSR HNLETALALE

GWLRLYGLSA                             610
```

Further, the phzH gene segment is from the genome of the *Pseudomonas aeruginosa* strain PAO1. As illustrated in the embodiments, the base sequence of the phzH gene segment is SEQ ID NO: 2.

```
gtccgaggac ccgtgcagcg ggccggtgtt cggtccgtcg    60
acctgcgaat gcccttgagg taggtcgtct ggcgggcccg gtgcagcggg cccgcttccg   120
gatgtatcgc tcgctcgaag ttgccttctt taattctcca ttccccgcgc cgccctactt   180
ttcccgctcg tccatcgtcg cgtcgaacgt tgccacgaaa tcagcgtcga tggacaactc   240
ttatattcaa tagttgtacg
```

-continued

```
atctgagttt gttgtagtca tttgcttagt tggctattca      300
tatgattgcc gtaaagcaac tataagttta attggattag ccttctaagt ctttggaaag      360
agccgtgaac gaccctgtaa tatctggttg tagagccgcg taatgatgtt tcaggatatt      420
tcattaattt tgtagattat tgtttttcct ttgttttttt aaaaacagct accagattta      480
gatagatatt aattaactcg gccacgtttt ttcctgttct atcattggcc ttccttgggc      540
gcaggcctgc cgaaactgct tatcttcagg tcctcgaaaa gttcatacat cgaccgcctt      600
gggcgaagca ttcgtacgcc ggaaatctgt ccggccgcac ggatgttttc agcatgttct      660
ctggatgagt ttcccgataa acatcaatta gaggagtttc cctatgtgcg gtctcgcggg      720
ttgggtggat tacacgcgca agctcgacga cgaatttccg gcgatcttcg ccatgaccga      780
tacgctcgcc atgcgcgggc cggatgccga gggcatctgg aagcaccgca acgccctgct      840
gggtcaccgg cggctggcgg tcatcgacct cagcggcggc gtgcagccga tgtcctatcg      900
ctttcccacc ggccaggagg tcaccctcgt ctacaccggc gaggtgtaca accacgatgc      960
cctgcgcgag cggttgcgcc gggccggaca tgagttccgc acccgcagcg ataccgaggt     1020
ggtcctgcac gcctatctgc aatggggcga gcgttgttgc gagtacctga ccgggatgtt     1080
cgccttcgcc gtcttcgatg gccgcgacgg ccacctgctg ctggtgcgcg accgcctggg     1140
catcaagccg ctgtattacg cgcggcaccg cgagggactg ctgttcggct cggagatcaa     1200
gtccatcctg gcgcatccgg aattcgccgc caggctcgac gcggtcggcc tggtcgacct     1260
cctgacgctg tcccggggca cttcgcagac gccgttccgc gaggtccagg aactgctgcc     1320
cggccacctg ctgtcctggc gtcccaattc ccaggcgaag ttgcgccgct attgggaggt     1380
acgccgccag gagcatgccg acgacctgca gagcaccgtg cagcgcaccc gcgaactggt     1440
cacccgcgcc ctggggcgc aattgcacgc cgacgttccg gtgtgttcgc tgctatcggg     1500
tgggctcgat tcgaccgccc tgaccggcat cgcccagcgc atcgcgaagg cggagcacgg     1560
cggcgacatc aattcattct cggtggactt cgtcggccag gccgagtagt tccgcagcga     1620
cgacctgcgt cccgaccagg accagccgtt cgccctgctg gccgcgcagt acatcggcag     1680
ccgtcatcgc accgtgctca tcgacaatgc cgaactggtc tgcgaacgag cgcgcgaaga     1740
ggtattccgg gccaaggacg tacctttcac cttcggcgac atggatacct cgctgcacct     1800
gatgttcggc gagatccgcc ggcattccac ggtggccatc tccggtgaag gcgccgacga     1860
gctgttcggt ggctacggct ggttccgcga tccgcaggcg gtggctgcgg cgcgcttccc     1920
ctgggcctcc agggtgcgcc tgccagccgg cttcatcgac gccggtttca accgccgctg     1980
cgatctcctc cagtaccagc aggccagcta cgacgatggg ctgcgccagg tcgaacacct     2040
ggccggcgac agcccggagg agcggcggat gcgcgagttc agccacctgc atctgaagcg     2100
ctggatggtg ctgctgctcg aacgcaagga tcgcctgagc atgtgcaacg gcctggaggt     2160
gcgggtgccc tacaccgacc atgagctggt ggagtacgtc tacaacgtgc cctggtcgat     2220
caagagccgg gacggcgagg agaagtggct gctcaagcgg gcctgcgccg actatgtccc     2280
ggaagccgtg ctcaagcgcc gcaagagccc ttatccgact tctgccaacc tcggctacga     2340
gcgtttcctg cgcgggagcg tgcggcgtct gctggaggac gcggcgaacc cggtgttcgg     2400
catcgtttcg cgagagttcc tggccgccga actggagcat ccggaggggt acttcaacac     2460
ccaggtgagc cgccacaacc tggagaccgc gctggcgctg gaaggctggc tcaggttgta     2516
cgggctctcc gcctga
```

The underlined and bold codons in the base sequence are the initiation codon and termination codon of the phzH gene respectively, and the bases before the initiation codon constitute the 5'-end noncoding region of the phzH gene.

Further, the expression vector for constructing the phzH gene recombination expression plasmid is an *Escherichia coli/Pseudomonas* shuttle expression plasmid.

In order that the phzH gene recombination expression plasmid can correctly express the phzH gene, it shall ensure that the phzH gene reading frame at the multiple clone site of the *Escherichia coli/Pseudomonas* shuttle expression plasmid is correct.

Preferably, to promote efficient expression of PhzH, the *Escherichia coli/Pseudomonas* shuttle expression plasmid comprises a strong promoter, the phzH gene segment is cloned behind the strong promoter, and the expression of the phzH gene segment is controlled by the strong promoter. The strong promoter may be a phage promoter T3 prom or T7 prom.

Insertion of a target gene in a specific site of the plasmid and ensuring the correct reading frame of the target gene are technologies well known by those skilled in the art. The *Escherichia coli/Pseudomonas* shuttle expression plasmid includes plasmids of pBBR1MCS series and derivative expression plasmids thereof. As illustrated in the embodiments, the *Escherichia coli/Pseudomonas* shuttle expression plasmid is pBBR1MCS-5. With a proper design of primers, the amplified phzH gene segment is under the control of the phage promoter T3 prom of pBBR1MCS-5 while ensuring the correct reading frame, thereby obtaining the gene recombination expression plasmid pBBRphzH.

The strain producing phenazine-1-carboxylic acid refers to a wild strain that produces phenazine-1-carboxylic acid through fermentation, as well as its derivative engineering strains. Further, the strain producing phenazine-1-carboxylic acid belongs to *Pseudomonas*, such as M18 and M18G.

The M18, with Deposition No. CGMCC NO.0462, is a bio-pesticide growth-promoting antagonistic bacterium, and phenazine-1-carboxylic acid, an active component for controlling plant diseases, can ben synthesized by living M18. M18 belongs to the prior art.

The M18G strain is a derivative strain of M18 (CGMCC NO.0462) and belongs to the prior art. The preparation method of M18G is known, for example, from Differential Regulation of Phenazine-1-Carboxylic Acid and Pyoluteorin Production Mediated by Inactivated gacA in *Pseudomonas* sp. M18, Acta Microbiologica Sinica, Vol. 44, p 761-765 in 2004. As compared with M18, the yield of phenazine-1-carboxylic acid in the case of M18G is greatly increased. Therefore, M18G is the preferred engineering strain producing phenazine-1-carboxylic acid in the present invention.

The wild strain producing phenazine-1-carboxylic acid and its derivative engineering strains can produce phenazine-1-carboxylic acid, the phzH gene recombination expression plasmid can express the phzH gene in the engineering strain producing phenazine-1-carboxylic acid, and the glutamine phenazine-1-carboxylic acid amidotransferase which is an encoding product of the phzH gene can amidate phenazine-1-carboxylic acid to synthesize phenazine-1-carboxamide (the molecular structural formula of phenazine-1-carboxamide is shown in FIG. 1). As such, the metabolites of the bioengineering strain of the present invention comprise phenazine-1-carboxamide.

The phzH gene recombination expression plasmid is introduced into the engineering strain producing phenazine-1-carboxylic acid by a conventional transformation or transduction method.

The bioengineering strain for production of microorganism-originated fungicides of the present invention can be used in production of the microorganism-originated fungicide of the present invention through fermentation.

The present invention further provides a microorganism-originated fungicide which is a fermentation broth of the bioengineering strain of the present invention.

The main fungicidal active component in the fermentation broth is phenazine-1-carboxamide. Also, the fermentation broth comprises a trace amount of pyoluteorin as a fungicidal active component.

Further, in the fermentation broth, the content of phenazine-1-carboxamide is 2500-2800 mg/L.

The present invention further discloses a preparation method of the microorganism-originated fungicide, where the microorganism-originated fungicide is obtained by fermenting and culturing the bioengineering strain of the present invention under conditions suitable for expression of phenazine-1-carboxylic acid and PhzH.

Further, the preparation method of the microorganism-originated fungicide comprises steps of:

1. activation of bioengineering strain;
2. inoculum enlargement: shake-flask culturing in a glycerol culture medium first and then transferring to a bacteriocin-producing culture medium for enlarged fermentation culturing to obtain the fermentation broth.

The activation of bioengineering strain may be conducted using a solid glycerol culture medium.

The glycerol culture medium comprises the following components in their respective weight percentages: 1.8-2.2% of peptone, 1.3-1.7% of glycerol, 0.05-0.1% of magnesium sulfate, 0.01-0.05% of potassium dihydrogen phosphate, the balance being water, pH 6.8-7.2.

The solid glycerol culture medium comprises the following components in their respective weight percentages: 1.8-2.2% of peptone, 1.3-1.7% of glycerol, 0.05-0.1% of magnesium sulfate, 0.01-0.05% of potassium dihydrogen phosphate, 1.2-1.5% of agar, the balance being water, pH 6.8-7.2.

The bacteriocin-producing culture medium comprises the following components in their respective weight percentages: 2.2-3.0% of peptone, 2.0-2.5% of glucose, 0.5-0.7% of potassium nitrate, the balance being water, pH 6.5-7.0.

Preferably, the engineering strain is activated as follows: the engineering strain is inoculated onto a plate with the glycerol culture medium where the engineering strain is activated and grows at 26-30° C. for 20-24 h; then, the strain mass is again streaked onto a plate with the glycerol culture medium, and activated at 26-30° C. for 10-12 h.

Preferably, in the inoculum enlargement, the shake-flask culturing in the glycerol culture medium is conducted as follows: the activated stain is inoculated into the glycerol culture medium where the strain is shake-cultured at 26-30° C. for 9-11 h. In shake-culturing, the rotation speed of the shaking table may be 160-180 rpm.

Preferably, in the inoculum enlargement, the enlarged fermentation culturing in the bacteriocin-producing culture medium is conducted as follows: the shake-cultured stain in the glycerol culture medium is transferred into the bacteriocin-producing culture medium where the strain is fermentation-cultured at 26-30° C. for 60-72 h. In fermentation culturing, the rotation speed of the shaking table may be 160-180 rpm.

The microorganism-originated fungicide of the present invention may be used in prophylaxis and treatment of plant diseases or in preparation of pesticides for prophylaxis and treatment of plant diseases.

Further, the microorganism-originated fungicide of the present invention is applied to crops by spraying or root irrigation for prophylaxis and treatment of rice sheath blight, rice bacterial leaf blight, rice false smut, wheat scab, cucumber blight disease, watermelon blight disease, melon gummy stem blight, cotton blight disease, anthrax, drooping disease, and plants diseases caused by *Pythium* or *Phytophthora*.

The present invention further discloses a pesticide for prophylaxis and treatment of plant diseases, which comprises a fungicidally effective amount of the microorganism-originated fungicide of the present invention or its fungicidal active components.

The fermentation broth of the bioengineering strain for production of microorganism-originated fungicides of the present invention may be directly used as a pesticide for prophylaxis and treatment of plant diseases. Also, the fermentation broth may also be dried into powder by a conventional method to be used as a fungicidal active component raw material to prepare pesticides for prophylaxis and treatment of plant diseases together with other conventional adjuvants. Alternatively, the major fungicidal active component phenazine-1-carboxamide in the fermentation broth may be isolated first and then used as a fungicidal active component raw material to prepare pesticides for prophylaxis and treatment of plant diseases.

The method of the present invention involving producing phenazine-1-carboxamide by utilizing an genetic engineering strain producing phenazine-1-carboxylic acid to carry a recombination expression vector has the following advantages:

1. The antifungal activity is stable and not influenced by acidity. The phenazine-1-carboxamide produced by the present invention not only has a high antifungal ability, but also is not influenced by the acidity of the environment at pH ranging from 4.0-8.0, so that it can provide a stable effect of prophylaxis and treatment whether it is used in crops planted in an acidic environment or in an alkaline environment.

2. Transformation efficiency is high. In the present invention, phenazine-1-carboxylic acid in the host is transformed into phenazine-1-carboxamide by constructing a gene recombination plasmid carrying the complete coding region of the phzH gene and its 5'-end noncoding region. In a preferred embodiment, the phzH gene and its 5'-end noncoding region are highly expressed under the control of the phage strong promoter T3 prom and meanwhile the recombination plasmid has multiple copies in the host M18G so that the phzH gene can be highly expressed and amidated enzyme can be synthesized in the host M18G and all phenazine-1-carboxylic acid is transformed into phenazine-1-carboxamide. As a result, the transformation efficiency may be as high as 100%.

3. Production cost is low and economic benefit is high. For production of phenazine-1-carboxamide by the present invention, apart from the one-off early cost consumed by preparation and construction of the engineering strain, once the industrialized production is started, additional incorporation of other raw materials and consumption of additional energy are not required other than consumption of culture medium. As such, with expansion and extension of production scale, the average production cost for unit yield is reduced significantly, which facilitates large-scale promotion and application in agricultural production.

4. Clean production and environment protection are achieved. Production of phenazine-1-carboxamide by a biotechnology can transform all phenazine-1-carboxylic acid into phenazine-1-carboxamide. In production, apart from consumption of culture medium, other special raw materials are not used and any other intermediates are not produced. As such, no new pollutants are produced and released into the environment, so that clear production is achieved and ecological environment is protected.

The present invention relates to a method for production of phenazine-1-carboxamide by utilizing an engineering stain M18G to carry plasmid pBBRphzH, where the segment of the phzH gene and its 5'-end noncoding region is amplified from the PAO1 genome of *Pseudomonas aeruginosa*, and this segment is then inserted into the expression plasmid pBBR1MCS-5 under the control of the phage promoter T3 prom so as to be constructed into pBBRphzH; the recombination plasmid is then transferred into the derivate strain M18G of the growth-promoting antagonistic bacterium M18 to construct a genetic engineering strain M18G/pBBRphzH which realizes the high and stable expression of glutamine phenazine-1-carboxylic acid amidotransferase (PhzH). Finally, the genetic engineering strain M18G/pBBRphzH is cultured in the culture medium to efficiently and stably produce phenazine-1-carboxamide. For the phenazine-1-carboxamide prepared by using the high-yield genetic engineering strain of the present invention, the effect of prophylaxis and treatment of disease is not influenced by acidity and its production cost is further reduced. Also, it is effective in prophylaxis and treatment of plants diseases whether it is used under acidic or alkaline conditions.

Figure 3:
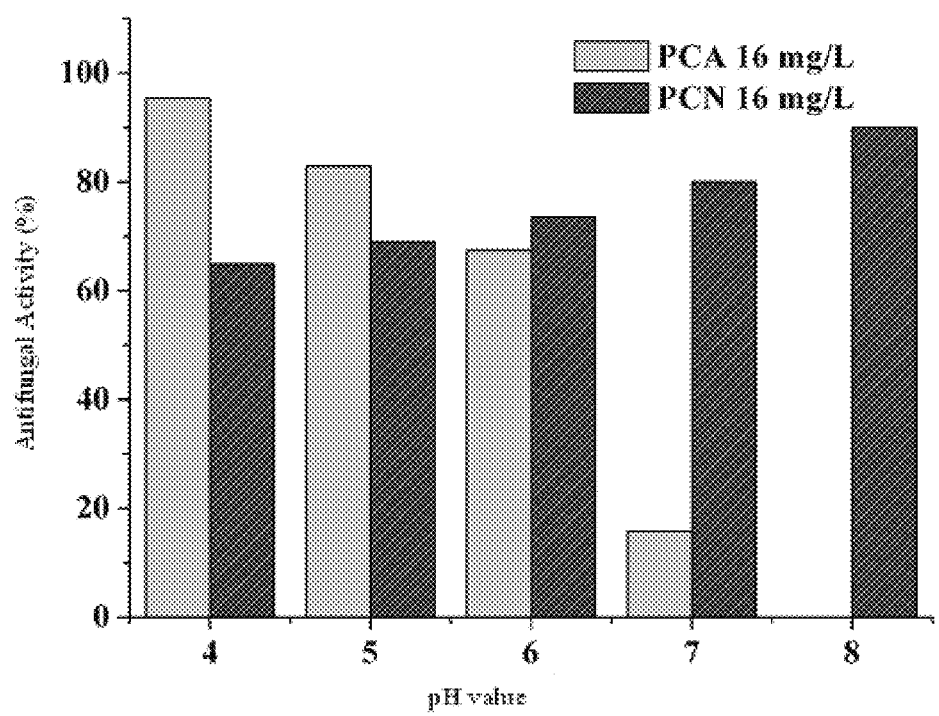

FIG. 3 shows the results of comparing the antifungal activities of phenazine-1-carboxylic acid (PCA) and phenazine-1-carboxamide (PCN) of the same concentration against *rhizoctonia solani* in potato glucose culture media under different acidities. In the experiment, the weight percentages of the components in the potato glucose culture medium are as follows: 20% of potato, 2% of glucose, 1.2% of agar powder, the balance being water.

DETAILED DESCRIPTION OF THE INVENTION

A preferred embodiment of the present invention utilizes the derivative strain M18G of the growth-promoting antagonistic strain M18 to carry the recombination plasmid pBBR-phzH to construct the genetic engineering strain M18G/pBBRphzH, where the copy number of the segment of the complete coding region of the phzH gene and its 5'-end noncoding region is complemented and added to transform phenazine-1-carboxylic acid into phenazine-1-carboxamide, thereby producing phenazine-1-carboxamide.

According to the preferred embodiment of the present invention, the segment of the complete coding region of the phzH gene and its 5'-end noncoding region is amplified from the PAO1 of *Pseudomonas aeruginosa* strains, and this segment is then inserted into the expression plasmid pBBR1MCS-5 so as to construct a recombination plasmid pBBRphzH while the segment is under the control of the phage promoter T3 prom; the recombination plasmid pBBR-phzH is then transferred into the derivate strain M18G of the growth-promoting antagonistic bacterium M18 to construct a genetic engineering strain M18G/pBBRphzH which realizes the high and stable expression of the phzH gene. Finally, the genetic engineering strain M18G/pBBRphzH is cultured in the culture medium to efficiently and stably produce phenazine-1-carboxamide instead of phenazine-1-carboxylic acid. The yield of phenazine-1-carboxamide reaches a level of 2500-2800 mg. Under pH equal to or greater than 7.0, the activity of phenazine-1-carboxamide against rice sheath blight is increased by more than 5 times relative to phenazine-1-carboxylic acid. As reckoned by this antifungal activity, the antifungal activity of phenazine-1-carboxamide produced per unit volume of the fermentation broth considerably exceeds the antifungal activity of phenazine-1-carboxylic acid.

A specific plan for constructing the genetic engineering strain M18G/pBBRphzH and utilizing this strain to produce phenazine-1-carboxamide is as follows:

1. Amplification of the Segment of the phzH Gene and its 5'-end Noncoding Region A pair of primers are designed, and the nucleotide sequences of the primers are as follows:

```
Forward:
                                       (SEQ ID NO: 3)
5'-CGCGCTCGAGGTCCGAGGACCCGTGCAGC-3'

Reverse:
                                       (SEQ ID NO: 4)
5'-CGCGAAGCTTTCAGGCGGAGAGCCCGTAC-3'
```

What are underlined in the sequences are cutting sites of restriction enzymes Xho I and Hind III; then with the PAO1 genomic DNA of *Pseudomonas aeruginosa* strains as a template, the segment of the phzH gene and its 5'-end noncoding region is amplified by using DNA polymerase LA Taq and the designed primers, and the amplification product is detected by agarose electrophoresis. The segment of the phzH gene and its 5'-end noncoding region of 2.5 kb long is recovered.

2. Construction of Recombinant Plasmid pBBRphzH

The recovered gene amplification segment phzH and its 5'-end noncoding region are digested by restriction enzymes Xho I and Hind III, and by the action of ligase, inserted into the corresponding cutting sites in the *Escherichia coli/Pseudomonas* shuttle expression plasmid pBBR1MCS-5, so that expression of the complete coding region of the phzH gene and its 5'-end noncoding region is under the control of the phage promoter T3 prom, thereby forming the recombination plasmid pBBRphzH which is then transformed into *Escherichia coli*; on a gentamicin resistant plate, *Escherichia coli* transformants transformed with pBBRphzH are screened out; the constructed gene recombination plasmid pBBRphzH is extracted from *Escherichia coli*.

3. Construction of Genetic Engineering Strain M18G/pBBRphzH

The competent cells of the derivative strain M18G of the growth-promoting antagonistic strain M18 are prepared, and the aforesaid gene recombination plasmid pBBRphzH is transformed into the competent cells of M18G which are then cultured at 28-37° C. for 1-2 d. The genetic engineering strain M18G/pBBRphzH is screened out from the culture.

4. Culturing of Genetic Engineering Strain M18G/pBBRphzH

The genetic engineering strain M18G/pBBRphzH is inoculated onto a plate with a glycerol culture medium where M18G/pBBRphzH is activated and grows at 26-30° C. for 20-24 h; then, the fungal mass is again streaked onto a plate with a glycerol culture medium and activated at 26-30° C. for 10-12 h. Then, the activated M18G/pBBRphzH fungal mass is transferred into a 250 ml triangular flask containing 25 ml of a glycerol culture medium, and shake-cultured on a shake table at 26-30° C. for 9-11 h, the rotation speed of the shaking table being 160-180 rpm; finally, the strain is transferred into a 500 ml triangular flask containing 65 ml of a bacteriocin-producing culture medium where the strain is enlarged fermentation-cultured for 60-72 h, the temperature and rotation speed being unchanged, thereby obtaining phenazine-1-carboxamide with a yield of 2500-2800 mg/L.

The present invention is to be further described below in conjunction with examples. It shall be understood that, these examples are only for the purpose of explaining the present invention rather than limiting the scope of the present invention. In the examples below, the experiment methods for which the specific conditions are not described and the reagents for which the formulas are not provided are all conducted or prepared according to conventional conditions such as conditions as described in Molecular Cloning: A Laboratory Manual or conditions as recommended by the manufacturer. The examples below are not limitations to the present invention.

Example 1

1. Amplification of Segment of the phzH Gene and its 5'-end Noncoding Region

A pair of primers were designed for amplification of the segment of the phzH gene and its 5'-end noncoding region, and the nucleotide sequences of the primers were as follows:

Forward:
5'-CGCG<u>CTCGAG</u>GTCCGAGGACCCGTGCAGC-3'

Reverse:
5'-CGCG<u>AAGCTT</u>TCAGGCGGAGAGCCCGTAC-3'

The underlined nucleotides in the sequences were cutting sites of restriction enzymes Xho I and Hind III. The primers were synthesized by Sangon Biotech (Shanghai) Co., Ltd.

Then, with the PAO1 genomic DNA of *Pseudomonas aeruginosa* strains as a template, the segment of the phzH gene and its 5'-end noncoding region was amplified by using the DNA polymerase LA Taq and the aforesaid designed primers, and the amplification product was detected by 0.7% agarose electrophoresis. The segment of the phzH gene and its 5'-end noncoding region of 2.5 kb long was recovered. The gene segment was verified correct by nucleotide sequencing. Specifically, the PAO1 genomic DNA of *Pseudomonas aeruginosa* was prepared by using an AxyPrep bacterial genomic DNA kit, and the gene segment was recovered using an AxyPrep DNA gel recovery kit. Both of the kits were provided by Axygen Biotechnology (Hangzhou) Co., Ltd with product catalog nos. of AP-MN-BT-GDNA-4 and AP-GX-50 respectively. The gene amplification and agarose electrophoresis were conducted according to the methods as described in p 611-618, Chapter 8 and p 387-400, Chapter 5 of Molecular Cloning: A Laboratory Manual (3rd edition) published by Science Press in 2002. Specifically, the DNA polymerase LA Taq and gene amplification kit was purchased from Shanghai Agency of TAKARA with a product catalog no. of DRR002AG, and the agarose was purchased from Shanghai Agency of GENE TECH. The nucleotide sequencing of the gene segment (phzH and its 5'-end noncoding region) was assigned to and completed by Invitrogen (Shanghai) Biotech Co., Ltd., and the sequencing results confirmed that the gene segment comprised SEQ ID NO: 2, and the amino acid sequence of the protein encoded by SEQ ID NO: 2 was SEQ ID NO: 1.

2. Construction of Recombinant Plasmid pBBRphzH

The recovered gene amplification segment (phzH and its 5'-end noncoding region) was digested by restriction enzymes Xho I and Hind III, and by the action of a ligase, inserted into the corresponding cutting sites in the *Escherichia coli/Pseudomonas* shuttle expression plasmid pBBR1MCS-5; expression of the segment of the phzH gene and its 5'-end noncoding region was under the control of phage promoter T3 prom, thereby forming a recombination plasmid pBBRphzH which was then transformed into *Escherichia coli*. On a gentamicin resistant plate, *Escherichia coli* transformants transformed with pBBRphzH were screened out. Finally, the constructed gene recombination plasmid pBBRphzH was extracted from the *Escherichia coli* transformants and verified.

Figure 1:
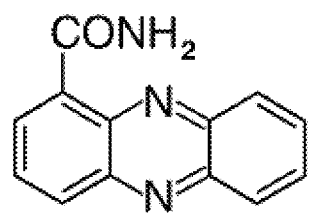
FIG. 1 is a molecular structural formula of phenazine-1-carboxamide in the present invention.
Figure 2:
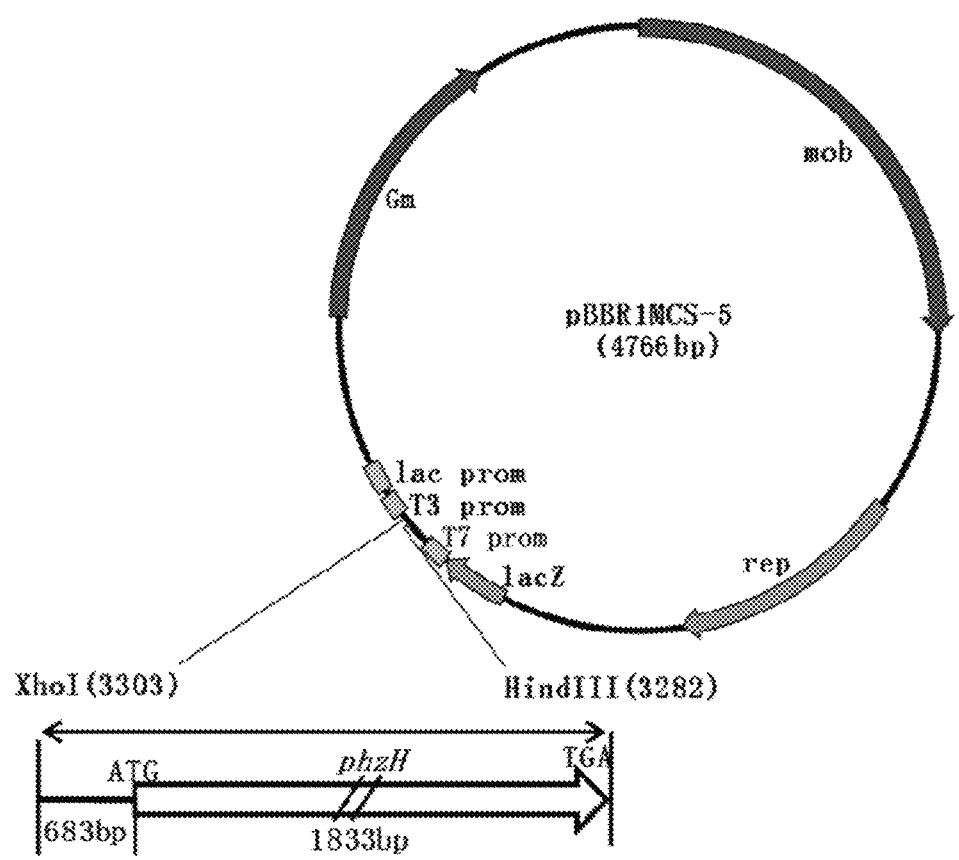
FIG. 2 is a schematic diagram for construction of the plasmid pBBRphzH in the present invention.

The constructed gene recombination plasmid pBBRphzH is as shown in FIG. 2, where the segment of the complete coding region comprising the phzH gene and its 5'-end noncoding region is digested by restriction enzymes Xho I and Hind III, and by the action of a ligase, inserted into the corresponding cutting sites in the *Escherichia coli/Pseudomonas* shuttle expression plasmid pBBR1MCS-5 to be under the control of the phage promoter T3 prom, thereby forming the recombination plasmid pBBRphzH. In FIG. 2, 4766 bp represents the length of the plasmid pBBR1MCS-5, which includes 4766 base pairs. In the figure, phzH represents glutamine phenazine-1-carboxylic acid amidotransferase encoding gene; // is a symbol indicating shortened gene segment; Xho I and Hind III are restriction enzyme cutting sites; and numerals in the figure indicate the lengths of the encoding sequence of the phzH gene and the nucleotide sequence of its 5'-end noncoding region ligated with plasmid pBBR1MCS-5, which are 1833 bp and 638 bp respectively; Gm is the selective marker gene resistant to gentamicin in the plasmid pBBR1MCS-5; T3 prom and T7 prom are two phage promoters; what is marked by mob is the gene required by plasmid transfer; what is marked by rep is the sequence required by plasmid replication; the gene indicated by lacZ encodes the α-peptide chain encoded by the lacZ' gene of *Escherichia coli*.

The aforesaid targeted insertion of gene segment into plasmid, preparation and transformation of competent *Escherichia coli*, and extraction and verification of recombination plasmid were carried out according to the methods as described in p 68-71 and p 96-99 Chapter 1, and p 663-666, Chapter 8 of Molecular Cloning: A Laboratory Manual (3rd edition) edited by J. Sambrook and D. W. Russell and published by Science Press in 2002. Specifically, the pBBR1MCS-5 plasmid was provided by the School of Life Sciences and Biotechnology, Shanghai Jiao Tong University. The restriction enzyme and ligase were purchased from Shenzhen Zhongjing Biotechnology Co., Ltd. The recombination plasmid in *Escherichia coli* was extracted using a type B plasmid extraction mini kit which was provided by Beijing Biodev-tech Scientific & Technical Co., Ltd with a product catalog no. of MK014-2. The restriction enzyme, DNA polymerase LA Taq and gene amplification kits used in verification of recombination plasmid were all purchased from Shanghai Agency of TAKARA with a product catalog no. of DRR002AG. The agarose was purchased from Shanghai Agency of GENE TECH.

3. Construction of Genetic Engineering Strain M18G/pBBRphzH

The competent cells of the derivative strain M18G of the growth-promoting antagonistic strain M18 were prepared, and the aforesaid gene recombination plasmid pBBRphzH was transformed into the competent cells of M18G which were then cultured at 28° C. for 2 d. The genetic engineering strain M18G/pBBRphzH was screened out from the culture.

The preparation of the competent cells of the derivative strain M18G of the growth-promoting antagonistic strain M18, transformation of recombination plasmid pBBRphzH into the competent cells of M18G, and screening of genetic engineering strain M18G/pBBRphzH for efficient production of phenazine-1-carboxamide were carried out according to the methods as described in p 96-99, Chapter 1 of Molecular Cloning: A Laboratory Manual (3rd edition) edited by J. Sambrook and D. W. Russell and published by Science Press in 2002.

4. Culturing of Genetic Engineering Strain M18G/pBBRphzH

The genetic engineering strain M18G/pBBRphzH was inoculated onto a plate with a glycerol culture medium where M18G/pBBRphzH was activated and grew at 26° C. for 24 h; then, the strain mass was again streaked onto a plate with a glycerol culture medium and activated at 26° C. for 10 h. Then, the activated M18G/pBBRphzH fungal mass was transferred into a 250 ml triangular flask containing 25 ml of a glycerol culture medium, and shake-cultured on a shake table at 26° C. for 9 h, the rotation speed of the shaking table being 160 rpm. Finally, the strain was transferred into a 500 ml special triangular flask containing 65 ml of a bacteriocin-producing culture medium where the strain was enlarged fermentation-cultured for 60 h, the temperature and rotation speed being unchanged, thereby obtaining phenazine-1-carboxamide with a yield of 2500 mg/L in the fermentation broth. The content of phenazine-1-carboxylic acid was not detected out, indicating that all phenazine-1-carboxylic acid had transformed into phenazine-1-carboxamide. As shown by the detection results, the rate of transformation of phenazine-1-carboxylic acid into phenazine-1-carboxamide was 100%.

Specifically, the glycerol culture medium comprised the following components in their respective weight percentages: 1.8% of peptone, 1.3% of glycerol, 0.07% of magnesium sulfate, 0.03% of potassium dihydrogen phosphate, the balance being water, pH 7.0. The glycerol culture medium (solid) further comprised 1.5% of agar. The bacteriocin-producing culture medium comprised the following components in their respective weight percentages: 2.2% of peptone, 2.0% of glucose, 0.5% of potassium nitrate, the balance being water, pH6.8.

With this formula, the 65 ml of M18G/pBBRphzH fermentation broth provided 162.5 mg of phenazine-1-carboxamide, the content of phenazine-1-carboxylic acid being zero. This fermentation broth was diluted proportionally to prepare a potato glucose culture medium (pH 7.0) containing 16 mg/ml phenazine-1-carboxamide. Also, an M18G/pME6032Phz fermentation broth (recorded in ZL200910198664.2) was diluted proportionally to prepare a potato glucose culture medium (pH 7.0) containing 16 mg/ml phenazine-1-carboxylic acid. With a potato glucose culture medium (pH 7.0) without any fermentation broth as a control, the growth rates of *Rhizoctonia solani* in the potato glucose culture media (pH 7.0) were measured respectively and the antifungal activities of phenazine-1-carboxamide and phenazine-1-carboxylic acid were calculated according to the method as described in Example 6. For bioactivity at the same pH of 7.0, the antifungal activity of phenazine-1-carboxamide obtained per liter of the M18G/pBBRphzH fermentation broth was equivalent to that of 12500 mg of phenazine-1-carboxylic acid, the antifungal activity being increased about 1.9 times.

Example 2

1. The complete coding region of the phzH gene and its 5'-end noncoding region were amplified by using the same method as in Example 1. The product was detected by 1.0% agarose electrophoresis and recovered to obtain the segment of the phzH gene and its 5'-end noncoding region of about 2.5 kb long.

2. The recovered segment of the phzH gene and its 5'-end noncoding region was digested by restriction enzymes Xho I and Hind III, and as ligated by a ligase, inserted into the *Escherichia coli/Pseudomonas* shuttle expression plasmid pBBR1MCS-5; expression of the segment of the phzH gene and its 5'-end noncoding region was under the control of the phage promoter T3 prom, thereby forming the recombination plasmid pBBRphzH which was then transformed into *Escherichia coli*. On a gentamicin resistant plate, *Escherichia coli* transformants transformed with pBBRphzH were screened out. Finally, the recombination plasmid was extracted from the *Escherichia coli* transformants and verified.

3. The competent cells of the derivative strain M18G of the growth-promoting antagonistic strain M18 were prepared, and the aforesaid recombination plasmid pBBRphzH was transformed into the competent cells of M18G which were then cultured at 30° C. for 1 d.

The preparation of the competent cells of the derivative strain M18G of the growth-promoting antagonistic strain M18, transformation of the recombination plasmid pBBRphzH into the competent cells of M18G, and screening of the genetic engineering strain M18G/pBBRphzH for efficient production of phenazine-1-carboxamide were all carried out according to the same methods as in Example 1.

4. The genetic engineering strain M18G/pBBRphzH was inoculated onto a plate with a glycerol culture medium where M18G/pBBRphzH was activated and grew at 28° C. for 22 h; then, the strain mass was again streaked onto a plate with a glycerol culture medium and activated at 28° C. for 11 h. Then, the activated M18G/pBBRphzH fungal mass was transferred into a 250 ml triangular flask containing 25 ml of a glycerol culture medium, and shake-cultured on a shake table at 28° C. for 10 h, the rotation speed of the shaking table being 170 rpm. Finally, the strain was transferred into a 500 ml triangular flask containing 65 ml of a bacteriocin-producing culture medium where the strain was enlarged fermentation-cultured for 66 h, the temperature and rotation speed being unchanged, thereby obtaining phenazine-1-carboxamide with a yield of 2700 mg/L in the fermentation broth. The content of phenazine-1-carboxylic acid was not detected out, indicating that all phenazine-1-carboxylic acid had transformed into phenazine-1-carboxamide. As shown by the detection results, the rate of transformation of phenazine-1-carboxylic acid into phenazine-1-carboxamide was 100%.

Specifically, the glycerol culture medium comprised the following components in their respective weight percentages: 2.2% of peptone, 1.7% of glycerol, 0.05% of magnesium sulfate, 0.01% of potassium dihydrogen phosphate, the balance being water, pH 7.2. The glycerol culture medium (solid) further comprised 1.5% of agar. The bacteriocin-producing culture medium comprised the following components in their respective weight percentages: 2.2% of peptone, 2.5% of glucose, 0.5% of potassium nitrate, the balance being water, pH7.2.

With this formula, the 65 ml of M18G/pBBRphzH fermentation broth provided 175.5 mg of phenazine-1-carboxamide, the content of phenazine-1-carboxylic acid being zero. This fermentation broth was diluted proportionally to prepare a potato glucose culture medium (pH 7.0) containing 16 mg/ml phenazine-1-carboxamide. Also, an M18G/pME6032Phz fermentation broth (recorded in ZL200910198664.2) was diluted proportionally to prepare a potato glucose culture medium (pH 7.0) containing 16 mg/ml phenazine-1-carboxylic acid. With a potato glucose culture medium (pH 7.0) without any fermentation broth as a control, the growth rates of rhizoctonia solani in the potato glucose culture media (pH 7.0) were measured respectively and the antifungal activities of phenazine-1-carboxamide and phenazine-1-carboxylic acid were calculated according to the method as described in Example 6. For bioactivity at the same pH of 7.0, the antifungal activity of phenazine-1-carboxamide obtained per liter of the M18G/pBBRphzH fermentation broth was equivalent to that of 13500 mg of phenazine-1-carboxylic acid, the antifungal activity being increased about 2.1 times.

Example 3

1. The complete coding region of the phzH gene and its 5'-end noncoding region were amplified by using the same method as in Example 1. The product was detected by 1.0% agarose electrophoresis and recovered to obtain the segment of the phzH gene and its 5'-end noncoding region of about 2.5 kb long.

2. The recovered segment of the phzH gene and its 5'-end noncoding region was digested by restriction enzymes Xho I and Hind III, and by the action of a ligase, inserted into the corresponding restriction enzyme cutting site of Escherichia coli/Pseudomonas shuttle expression plasmid pBBR1MCS-5 to be under the control of the phage promoter T3 prom, thereby forming the recombination plasmid pBBRphzH which was then transformed into Escherichia coli. On a gentamicin resistant plate, Escherichia coli transformants transformed with pBBRphzH were screened out. Finally, the recombination plasmid was extracted from the Escherichia coli and verified.

3. The competent cells of the derivative strain M18G of the growth-promoting antagonistic strain M18 were prepared, and the aforesaid recombination plasmid pBBRphzH was transformed into the competent cells of M18G which were then cultured at 32° C. for 2 d, and then from which the genetic engineering strain M18G/pBBRphzH for efficient production of phenazine-1-carboxamide was screen out.

The preparation of the competent cells of the derivative strain M18G of the growth-promoting antagonistic strain M18, transformation of the recombination plasmid pBBRphzH into the competent cells of M18G, and screening of the genetic engineering strain M18G/pBBRphzH for efficient production of phenazine-1-carboxamide were all carried out according to the same methods as in Example 1.

4. The genetic engineering strain M18G/pBBRphzH constructed by the gene engineering technology was inoculated onto a plate with a glycerol culture medium where M18G/pBBRphzH was activated and grew at 30° C. for 20 h; then, the strain mass was again streaked onto a plate with a glycerol culture medium and activated at 30° C. for 12 h. Then, the activated M18G/pBBRphzH strain was transferred into a 250 ml triangular flask containing 25 ml of a glycerol culture medium, and shake-cultured on a shake table at 30° C. for 11 h, the rotation speed of the shaking table being 180 rpm. Finally, the strain was transferred into a 500 ml triangular flask containing 65 ml of a bacteriocin-producing culture medium where the strain was enlarged fermentation-cultured for 72 h, the temperature and rotation speed being unchanged, thereby obtaining phenazine-1-carboxamide with a yield of 2800 mg/L in the fermentation broth. The content of phenazine-1-carboxylic acid was not detected out, indicating that all phenazine-1-carboxylic acid had transformed into phenazine-1-carboxamide. As shown by the detection results, the rate of transformation of phenazine-1-carboxylic acid into phenazine-1-carboxamide was 100%.

Specifically, the glycerol culture medium comprised the following components in their respective weight percentages: 2.0% of peptone, 1.5% of glycerol, 0.1% of magnesium sulfate, 0.05% of potassium dihydrogen phosphate, the balance being water, pH 6.8. The glycerol culture medium (solid) further comprised 1.5% of agar. The bacteriocin-producing culture medium comprised the following components in their respective weight percentages: 3.0% of peptone, 2.5% of glucose, 0.8% of potassium nitrate, the balance being water, pH7.0.

With this formula, the 65 ml of M18G/pBBRphzH fermentation broth provided 182 mg of phenazine-1-carboxamide, the content of phenazine-1-carboxylic acid being zero. This fermentation broth was diluted proportionally to prepare a potato glucose culture medium (pH 7.0) containing 16 mg/ml phenazine-1-carboxamide. Also, an M18G/pME6032Phz fermentation broth (recorded in ZL200910198664.2) was diluted proportionally to prepare a potato glucose culture medium (pH 7.0) containing 16 mg/ml phenazine-1-carboxylic acid. With a potato glucose culture medium (pH 7.0) without any fermentation broth as a control, the growth rates of rhizoctonia solani were measured respectively and the antifungal activities of phenazine-1-carboxamide and phenazine-1-carboxylic acid were calculated according to the method as described in Example 6. For bioactivity at the same pH of 7.0, the antifungal activity of phenazine-1-carboxamide obtained per liter of the M18G/pBBRphzH fermentation broth was equivalent to that of 14000 mg of phenazine-1-carboxylic acid, the antifungal activity being increased about 2.2 times.

Example 4

1. The complete coding region of the phzH gene and its 5'-end noncoding region were amplified by using the same method as in Example 1. The product was detected by 1.0% agarose electrophoresis and recovered to obtain the segment of the phzH gene and its 5'-end noncoding region of about 2.5 kb long.

2. The recovered segment of the phzH gene and its 5'-end noncoding region was digested by restriction enzymes Xho I and Hind III, and by the action of a ligase, inserted into the corresponding restriction enzyme cutting site of *Escherichia coli/Pseudomonas* shuttle expression plasmid pBBR1MCS-5 to be under the control of the phage promoter T3 prom, thereby forming the recombination plasmid pBBRphzH which was then transformed into *Escherichia coli*. On a gentamicin resistant plate, *Escherichia coli* transformants transformed with pBBRphzH were screened out. Finally, the recombination plasmid was extracted from the *Escherichia coli* and verified.

3. The competent cells of the derivative strain M18G of the growth-promoting antagonistic strain M18 were prepared, and the aforesaid recombination plasmid pBBRphzH was transformed into the competent cells of M18G which were then cultured at 32° C. for 2 d, and then from which the genetic engineering strain M18G/pBBRphzH for production of phenazine-1-carboxamide was screen out.

The preparation of the competent cells of the derivative strain M18G of the growth-promoting antagonistic strain M18, transformation of the recombination plasmid pBBRphzH into the competent cells of M18G, and screening of the genetic engineering strain M18G/pBBRphzH for production of phenazine-1-carboxamide were all carried out according to the methods as described in p 96-99, Chapter 1 of Molecular Cloning: A Laboratory Manual (3rd edition) edited by J. Sambrook and D. W. Russell and published by Science Press in 2002.

4. The genetic engineering strain M18G/pBBRphzH constructed by the gene engineering technology was inoculated onto a plate with a glycerol culture medium where M18G/pBBRphzH was activated and grew at 30° C. for 20 h; then, the bacterial mass was again streaked onto a plate with a glycerol culture medium and activated at 30° C. for 12 h. Then, the activated M18G/pBBRphzH strain was transferred into a 250 ml triangular flask containing 25 ml of a glycerol culture medium, and shake-cultured on a shake table at 30° C. for 11 h, the rotation speed of the shaking table being 180 rpm. Finally, the strain was transferred into a 500 ml triangular flask containing 65 ml of a bacteriocin-producing culture medium where the strain was enlarged fermentation-cultured for 72 h, the temperature and rotation speed being unchanged, thereby obtaining phenazine-1-carboxamide with a yield of 300 mg/L in the fermentation broth. The content of phenazine-1-carboxylic acid was not detected out.

Specifically, the components of the glycerol culture medium and the bacteriocin-producing culture medium were the same as in Example 1.

With this formula, the yield of phenazine-1-carboxamide was 300 mg/L. The content of phenazine-1-carboxylic acid was zero, indicating that all phenazine-1-carboxylic acid had transformed into phenazine-1-carboxamide. As shown by the detection results, in the engineering strain M18/pBBR-phzH, the rate of transformation of phenazine-1-carboxylic acid into phenazine-1-carboxamide was 100%.

Example 5

1. The complete coding region of the phzH gene and its 5'-end noncoding region were amplified by using the same method as in Example 1. The product was detected by 1.0% agarose electrophoresis and recovered to obtain the segment of the phzH gene and its 5'-end noncoding region of about 2.5 kb long.

2. The recovered segment of the phzH gene and its 5'-end noncoding region was digested by restriction enzymes Xho I and Hind III, and by the action of a ligase, inserted into the corresponding restriction enzyme cutting site of *Escherichia coli/Pseudomonas* shuttle expression plasmid pBBR1MCS-5, so that expression of the phzH gene was under the control of the phage promoter T3 prom, thereby forming the recombination plasmid pBBRphzH which was then transformed into *Escherichia coli*. On a gentamicin resistant plate, *Escherichia coli* transformants transformed with pBBR-phzH were screened out. Finally, the recombination plasmid was extracted from the *Escherichia coli* and verified.

3. The competent cells of the *Pseudomonas* PAO1 strain were prepared, and the aforesaid recombination plasmid pBBRphzH was transformed into the competent cells of PAO1 which were then cultured at 32° C. for 2 d, and then from which the genetic engineering strain PAO1/pBBRphzH for production of phenazine-1-carboxamide was screen out.

The preparation of the competent cells of the *Pseudomonas* PAO1 strain, transformation of the recombination plasmid pBBRphzH into the competent cells of PAO1, and screening of the genetic engineering strain PAO1/pBBR-phzH for production of phenazine-1-carboxamide were all carried out according to the methods as described in p 96-99, Chapter 1 of Molecular Cloning: A Laboratory Manual (3rd edition) edited by J. Sambrook and D. W. Russell and published by Science Press in 2002.

4. The genetic engineering strain PAO1/pBBRphzH constructed by the gene engineering technology was inoculated onto a plate with a glycerol culture medium where M18G/pBBRphzH was activated and grew at 30° C. for 20 h; then, the bacterial mass was again streaked onto a plate with a glycerol culture medium and activated at 30° C. for 12 h. Then, the activated PAO1/pBBRphzH strain was transferred into a 250 ml triangular flask containing 25 ml of a glycerol culture medium, and shake-cultured on a shake table at 30° C. for 11 h, the rotation speed of the shaking table being 180 rpm. Finally, the strain was transferred into a 500 ml triangular flask containing 65 ml of a bacteriocin-producing culture medium where the strain was enlarged fermentation-cultured for 72 h, the temperature and rotation speed being unchanged, thereby obtaining phenazine-1-carboxamide with a yield of 50 mg/L in the fermentation broth. The content of phenazine-1-carboxylic acid was not detected out.

Specifically, the components of the glycerol culture medium and the bacteriocin-producing culture medium were the same as in Example 1.

With this formula, the yield of phenazine-1-carboxamide was 50 mg/L. The content of phenazine-1-carboxylic acid was not detected out, indicating that all phenazine-1-carboxylic acid had transformed into phenazine-1-carboxamide. As shown by the detection results, in the engineering strain PAO1/pBBRphzH, the rate of transformation of phenazine-1-carboxylic acid into phenazine-1-carboxamide was 100%.

Example 6

Detection of Stability in Antifungal Activity of phenazine-1-carboxamide as Fermentation Product The acidity of a potato glucose culture medium was adjusted with a phosphate-citrate buffer to 4.0, 5.0, 6.0, 7.0, and 8.0 respectively. To the potato glucose culture media with different acidities, a certain amount of each of an M18G/pME6032Phz fermentation broth and an M18G/pBBRphzH fermentation broth was added respectively, thereby obtaining potato glucose culture media with diluted 16 mg/L of phenazine-1-carboxylic acid and phenazine-1-carboxamide respectively having different acidities. The potato glucose culture media were then poured into 9 cm diameter petri dishes to form flat plates, a potato glucose culture medium plate without any fermentation broth was used as a blank control, and each treatment had three repetitions. A rice sheath blight pathogenic hypha mass with a diameter of 8 mm was inoculated at the center of the plate, and incubated in a thermostatic incubator at 28° C. Once the pathogenic hyphae in the blank control grew all over the petri dish, the diameters of the fungal masses inoculated in the potato glucose culture media were respectively measured by using the crossing method. Antifungal rate, that is inhibition rate of fungal growth is calculated as follows: antifungal rate= $(1-(D^2-D_{in}^2)/(D_{ck}^2-D_{in}^2))\times 100\%$, where D represents the average diameter of the hypha mass in the treatment group; $D_{in}$ represents the initial diameter of the hypha mass; $D_{ck}$ represents the average diameter of the hypha mass in the control. The analysis results are shown in FIG. 3, wherein PCA represents phenazine-1-carboxylic acid, and PCN represents phenazine-1-carboxamide. The results show that, under acidities of 4.0, 5.0, 6.0, 7.0, 8.0, the antifungal activities of phenazine-1-carboxylic acid (PCA) against rhizoctonia solani were 95.5%, 82.9%, 67.5%, 15.9%, and 0 respectively; the antifungal activities of phenazine-1-carboxamide (PCN) against rhizoctonia solani were 65%, 69%, 73.6%, 80.1%, and 90% respectively. That is, under pH of 4-8, as compared with phenazine-1-carboxylic acid, the antifungal rate of phenazine-1-carboxamide against rhizoctonia solani was stable; meanwhile, under pH of 7.0, the antifungal activity of phenazine-1-carboxamide against Rhizoctonia solani was 5 times that of phenazine-1-carboxylic acid.

Specifically, the potato glucose culture medium comprised the following components in their respective weight percentages: 20% of potato, 2% of glucose, 1.5% of agar, the balance being water.

What is claimed is:

1. A bioengineering strain for production of microorganism-originated fungicides, wherein the bioengineering strain is obtained by transforming a phzH gene expression plasmid into a strain producing phenazine-1-carboxylic acid, wherein the bioengineering strain produces phenazine-1-carboxamide; the phzH gene expression plasmid is an expression plasmid cloned with a phzH gene fragment; the phzH gene expression plasmid expresses phzH gene in the strain producing phenazine-1-carboxylic acid where the phzH gene is encoded to produce PhzH (glutamine phenazine-1-carboxylic acid amidotransferase), the amino acid sequence of the PhzH is SEQ ID NO:1; the PhzH is a PhzH of *Pseudomonas aeruginosa* strains PAO1, and the phzH gene segment is a phzH gene segment of *Pseudomonas aeruginosa* strains PAO1; the nucleotide base sequence of the phzH gene fragment comprises a complete coding region of the phzH gene and a 5'-end noncoding region; the sequence of the 5'-end noncoding region comprises a polynucleotide segment starting from the first nucleotide base to the 683th nucleotide base of SEQ ID NO:2; and the strain producing phenazine-1-carboxylic acid is a growth-promoting antagonistic bacterium M18 or an engineering strain M18G.

2. The bioengineering strain of claim 1, wherein the nucleotide base sequence of the phzH gene segment is SEQ ID NO: 2.

3. The bioengineering strain of claim 1, wherein an expression vector for constructing the phzH gene expression plasmid is an *Escherichia coli/Pseudomonas* shuttle expression plasmid.

4. The bioengineering strain of claim 3, wherein the *Escherichia coli/Pseudomonas* shuttle expression plasmid comprises a strong promoter, the phzH gene segment is cloned behind the strong promoter, and expression of the phzH gene segment is controlled by the strong promoter.

5. The bioengineering strain of claim 4, wherein the *Escherichia coli/Pseudomonas* shuttle expression plasmid includes plasmids of pBBR1MCS series.

6. The bioengineering strain of claim 5, wherein the *Escherichia coli/Pseudomonas* shuttle expression plasmid is pBBR1MCS-5 and the phzH gene is controlled by a phage promoter T3 of the pBBR1MCS-5 on the premise of ensuring a correct reading frame.

7. The bioengineering strain of claim 1 for use in the production of microorganism-originated fungicides through fermentation.

8. A microorganism-originated fungicide, which is a fermentation broth of the bioengineering strain of claim 1.

9. The microorganism-originated fungicide of claim 8, comprising the main fungicidal active component of the fermentation broth comprises phenazine-1-carboxamide.

10. The microorganism-originated fungicide of claim 9, which is in the fermentation broth, and the content of phenazine-1-carboxamide is 2500-2800 mg/L.

11. The microorganism-originated fungicide of claim 8, comprising the microorganism-originated fungicide which is obtained by fermenting and culturing the bioengineering strain of any one of claims 1, 4-5 and 6 under conditions suitable for expression of PhzH and production of phenazine-1-carboxylic acid.

12. A pesticide composition for prophylaxis and treatment of plant diseases, which comprises a fungicidally effective amount of the microorganism-originated fungicide of claim 8 or a fungicidally active component from the microorganism-originated fungicide of claim 8.

* * * * *

SEQUENCE LISTING

```
<160> NUMBER OF SEQ ID NOS: 4

<210> SEQ ID NO 1
<211> LENGTH: 610
<212> TYPE: PRT
<213> ORGANISM: Pseudomonas aeruginosa

<400> SEQUENCE: 1

Met Cys Gly Leu Ala Gly Trp Val Asp Tyr Thr Arg Lys Leu Asp Asp
1               5                   10                  15

Glu Phe Pro Ala Ile Phe Ala Met Thr Asp Thr Leu Ala Leu Arg Gly
            20                  25                  30

Pro Asp Ala Glu Gly Ile Trp Lys His Arg Asn Ala Leu Leu Gly His
        35                  40                  45

Arg Arg Leu Ala Val Ile Asp Leu Ser Gly Gly Val Gln Pro Met Ser
    50                  55                  60

Tyr Arg Phe Pro Thr Gly Gln Glu Val Thr Leu Val Tyr Thr Gly Glu
65                  70                  75                  80

Val Tyr Asn His Asp Ala Leu Arg Glu Arg Leu Arg Arg Ala Gly His
                85                  90                  95

Glu Phe Arg Thr Arg Ser Asp Thr Glu Val Val Leu His Ala Tyr Leu
            100                 105                 110

Gln Trp Gly Glu Arg Cys Cys Glu Tyr Leu Thr Gly Met Phe Ala Phe
        115                 120                 125

Ala Val Phe Asp Gly Arg Asp Gly His Leu Leu Leu Val Arg Asp Arg
    130                 135                 140

Leu Gly Ile Lys Pro Leu Tyr Tyr Ala Arg His Arg Glu Gly Leu Leu
145                 150                 155                 160

Phe Gly Ser Glu Ile Lys Ser Ile Leu Ala His Pro Glu Phe Ala Ala
                165                 170                 175
```

```
Arg Leu Asp Ala Val Gly Leu Val Asp Leu Leu Thr Leu Ser Arg Gly
            180                 185                 190

Thr Ser Gln Thr Pro Phe Arg Glu Val Gln Glu Leu Leu Pro Gly His
        195                 200                 205

Leu Leu Ser Trp Arg Pro Asn Ser Gln Ala Lys Leu Arg Arg Tyr Trp
210                 215                 220

Glu Val Arg Arg Gln Glu His Ala Asp Asp Leu Gln Ser Thr Val Gln
225                 230                 235                 240

Arg Thr Arg Glu Leu Val Thr Arg Ala Leu Gly Ala Gln Leu His Ala
                245                 250                 255

Asp Val Pro Val Cys Ser Leu Leu Ser Gly Gly Leu Asp Ser Thr Ala
                260                 265                 270

Leu Thr Gly Ile Ala Gln Arg Ile Ala Lys Ala Glu His Gly Gly Asp
            275                 280                 285

Ile Asn Ser Phe Ser Val Asp Phe Val Gly Gln Ala Glu Gln Phe Arg
        290                 295                 300

Ser Asp Asp Leu Arg Pro Asp Gln Asp Pro Phe Ala Leu Leu Ala
305                 310                 315                 320

Ala Gln Tyr Ile Gly Ser Arg His Arg Thr Val Leu Ile Asp Asn Ala
                325                 330                 335

Glu Leu Val Cys Glu Arg Ala Arg Glu Val Phe Arg Ala Lys Asp
                340                 345                 350

Val Pro Phe Thr Phe Gly Asp Met Asp Thr Ser Leu His Leu Met Phe
            355                 360                 365

Gly Glu Ile Arg Arg His Ser Thr Val Ala Ile Ser Gly Glu Gly Ala
        370                 375                 380

Asp Glu Leu Phe Gly Gly Tyr Gly Trp Phe Arg Asp Pro Gln Ala Val
385                 390                 395                 400

Ala Ala Ala Arg Phe Pro Trp Ala Ser Arg Val Arg Leu Pro Ala Gly
                405                 410                 415

Phe Ile Asp Ala Gly Phe Asn Arg Arg Cys Asp Leu Leu Gln Tyr Gln
            420                 425                 430

Gln Ala Ser Tyr Asp Asp Gly Leu Arg Gln Val Glu His Leu Ala Gly
        435                 440                 445

Asp Ser Pro Glu Glu Arg Arg Met Arg Glu Phe Ser His Leu His Leu
450                 455                 460

Lys Arg Trp Met Val Leu Leu Glu Arg Lys Asp Arg Leu Ser Met
465                 470                 475                 480

Cys Asn Gly Leu Glu Val Arg Val Pro Tyr Thr Asp His Glu Leu Val
                485                 490                 495

Glu Tyr Val Tyr Asn Val Pro Trp Ser Ile Lys Ser Arg Asp Gly Glu
            500                 505                 510

Glu Lys Trp Leu Leu Lys Arg Ala Cys Ala Asp Tyr Val Pro Glu Ala
        515                 520                 525

Val Leu Lys Arg Arg Lys Ser Pro Tyr Pro Thr Ser Ala Asn Leu Gly
            530                 535                 540

Tyr Glu Arg Phe Leu Arg Gly Ser Val Arg Leu Leu Glu Asp Ala
545                 550                 555                 560

Val Asn Pro Val Phe Gly Ile Val Ser Arg Glu Phe Leu Ala Ala Glu
                565                 570                 575

Leu Glu His Pro Glu Gly Tyr Phe Asn Thr Gln Val Ser Arg His Asn
                580                 585                 590
```

Leu Glu Thr Ala Leu Ala Leu Glu Gly Trp Leu Arg Leu Tyr Gly Leu
    595                 600                 605

Ser Ala
    610

<210> SEQ ID NO 2
<211> LENGTH: 2516
<212> TYPE: DNA
<213> ORGANISM: Pseudomonas aeruginosa

<400> SEQUENCE: 2

| | | | | | |
|---|---|---|---|---|---|
| gtccgaggac | ccgtgcagcg | ggccggtgtt | cggtccgtcg | acctgcgaat | gcccttgagg | 60 |
| taggtcgtct | ggcgggcccg | gtgcagcggg | cccgcttccg | gatgtatcgc | tcgctcgaag | 120 |
| ttgccttctt | taattctcca | ttccccgcgc | cgccctactt | ttcccgctcg | tccatcgtcg | 180 |
| cgtcgaacgt | tgccacgaaa | tcagcgtcga | tggacaactc | ttatattcaa | tagttgtacg | 240 |
| atctgagttt | gttgtagtca | tttgcttagt | tggctattca | tatgattgcc | gtaaagcaac | 300 |
| tataagttta | attggattag | ccttctaagt | ctttggaaag | agccgtgaac | gaccctgtaa | 360 |
| tatctggttg | tagagccgcg | taatgatgtt | tcaggatatt | tcattaattt | tgtagattat | 420 |
| tgtttttcct | ttgttttttt | aaaaacagct | accagattta | gatagatatt | aattaactcg | 480 |
| gccacgtttt | ttcctgttct | atcattggcc | ttccttgggc | gcaggcctgc | cgaaactgct | 540 |
| tatcttcagg | tcctcgaaaa | gttcatacat | cgaccgcctt | gggcgaagca | ttcgtacgcc | 600 |
| ggaaatctgt | ccggccgcac | ggatgttttc | agcatgttct | ctggatgagt | ttcccgataa | 660 |
| acatcaatta | gaggagtttc | cctatgtgcg | gtctcgcggg | ttgggtggat | tacacgcgca | 720 |
| agctcgacga | cgaatttccg | gcgatcttcg | ccatgaccga | tacgctcgcc | atgcgcgggc | 780 |
| cggatgccga | gggcatctgg | aagcaccgca | acgccctgct | gggtcaccgg | cggctggcgg | 840 |
| tcatcgacct | cagcggcggc | gtgcagccga | tgtcctatcg | ctttcccacc | ggccaggagg | 900 |
| tcaccctcgt | ctacaccggc | gaggtgtaca | ccacgatgc | cctgcgcgag | cggttgcgcc | 960 |
| gggccggaca | tgagttccgc | acccgcagcg | ataccgaggt | ggtcctgcac | gcctatctgc | 1020 |
| aatggggcga | gcgttgttgc | gagtacctga | ccgggatgtt | cgccttcgcc | gtcttcgatg | 1080 |
| gccgcgacgg | ccacctgctg | ctggtgcgcg | accgcctggg | catcaagccg | ctgtattacg | 1140 |
| cgcggcaccg | cgagggactg | ctgttcggct | cggagatcaa | gtccatcctg | cgcatccgg | 1200 |
| aattcgccgc | caggctcgac | gcggtcggcc | tggtcgacct | cctgacgctg | tcccggggca | 1260 |
| cttcgcagac | gccgttccgc | gaggtccagg | aactgctgcc | cggccacctg | ctgtcctggc | 1320 |
| gtcccaattc | ccaggcgaag | ttgcgccgct | attgggaggt | acgccgccag | gagcatgccg | 1380 |
| acgacctgca | gagcaccgtg | cagcgcaccc | gcgaactggt | cacccgcgcc | ctggggcgc | 1440 |
| aattgcacgc | cgacgttccg | gtgtgttcgc | tgctatcggg | tgggctcgat | tcgaccgccc | 1500 |
| tgaccggcat | cgcccagcgc | atcgcgaagg | cggagcacgg | cggcgacatc | aattcattct | 1560 |
| cggtggactt | cgtcggccag | gccgagtagt | tccgcagcga | cgacctgcgt | cccgaccagg | 1620 |
| accagccgtt | cgccctgctg | gccgcgcagt | acatcggcag | ccgtcatcgc | accgtgctca | 1680 |
| tcgacaatgc | cgaactggtc | tgcgaacgag | cgcgcgaaga | ggtattccgg | gccaaggacg | 1740 |
| tacctttcac | cttcggcgac | atggatacct | cgctgcacct | gatgttcggc | gagatccgcc | 1800 |
| ggcattccac | ggtggccatc | tccggtgaag | gcgccgacga | gctgttcggt | ggctacggct | 1860 |
| ggttccgcga | tccgcaggcg | gtggctgcgg | cgcgcttccc | ctgggcctcc | agggtgcgcc | 1920 |
| tgccagccgg | cttcatcgac | gccggtttca | accgccgctg | cgatctcctc | cagtaccagc | 1980 |

-continued

```
aggccagcta cgacgatggg ctgcgccagg tcgaacacct ggccggcgac agcccggagg    2040
agcggcggat gcgcgagttc agccacctgc atctgaagcg ctggatggtg ctgctgctcg    2100
aacgcaagga tcgcctgagc atgtgcaacg gcctggaggt gcgggtgccc tacaccgacc    2160
atgagctggt ggagtacgtc tacaacgtgc cctggtcgat caagagccgg gacggcgagg    2220
agaagtggct gctcaagcgg gcctgcgccg actatgtccc ggaagccgtg ctcaagcgcc    2280
gcaagagccc ttatccgact tctgccaacc tcggctacga gcgtttcctg cgcgggagcg    2340
tgcggcgtct gctggaggac gcggcgaacc cggtgttcgg catcgtttcg cgagagttcc    2400
tggccgccga actggagcat ccggaggggt acttcaacac ccaggtgagc cgccacaacc    2460
tggagaccgc gctggcgctg gaaggctggc tcaggttgta cgggctctcc gcctga        2516
```

```
<210> SEQ ID NO 3
<211> LENGTH: 29
<212> TYPE: DNA
<213> ORGANISM: artificial sequence
<220> FEATURE:
<223> OTHER INFORMATION: Primer

<400> SEQUENCE: 3
cgcgctcgag gtccgaggac ccgtgcagc                                      29

<210> SEQ ID NO 4
<211> LENGTH: 29
<212> TYPE: DNA
<213> ORGANISM: artificial sequence
<220> FEATURE:
<223> OTHER INFORMATION: Primer

<400> SEQUENCE: 4
cgcgaagctt tcaggcggag agcccgtac                                      29
```